United States Patent
Cherry et al.

(10) Patent No.: US 10,058,631 B2
(45) Date of Patent: Aug. 28, 2018

(54) TONSILLECTOMY SPONGE

(71) Applicant: Cook Medical Technologies LLC, Bloomington, IN (US)

(72) Inventors: Thomas Cherry, Covington, LA (US); Melissa Rose Taylor, Willowick, OH (US); Don Patterson, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 330 days.

(21) Appl. No.: 14/795,001

(22) Filed: Jul. 9, 2015

(65) Prior Publication Data
US 2016/0008513 A1 Jan. 14, 2016

Related U.S. Application Data

(60) Provisional application No. 62/022,243, filed on Jul. 9, 2014.

(51) Int. Cl.
| | |
|---|---|
| A61F 2/00 | (2006.01) |
| A61L 27/36 | (2006.01) |
| A61L 27/56 | (2006.01) |
| A61L 27/54 | (2006.01) |
| A61B 17/00 | (2006.01) |
| A61B 17/26 | (2006.01) |

(52) U.S. Cl.
CPC ...... *A61L 27/3633* (2013.01); *A61B 17/0057* (2013.01); *A61L 27/3641* (2013.01); *A61L 27/54* (2013.01); *A61L 27/56* (2013.01); *A61B 17/26* (2013.01); *A61B 2017/00632* (2013.01); *A61B 2017/00654* (2013.01); *A61B 2017/00659* (2013.01); *A61B 2017/00884* (2013.01); *A61B 2017/00898* (2013.01); *A61L 2300/414* (2013.01); *A61L 2430/34* (2013.01)

(58) Field of Classification Search
CPC .................................. A61F 2/00; A61L 15/58
USPC .......... 623/14.12, 23.57, 23.61, 23.63, 23.72
See application file for complete search history.

(56) References Cited

U.S. PATENT DOCUMENTS

| | | | | |
|---|---|---|---|---|
| 2003/0036797 | A1* | 2/2003 | Malaviya | A61B 17/064 623/14.12 |
| 2014/0148914 | A1* | 5/2014 | Mohan | A61B 17/26 623/23.72 |
| 2014/0343688 | A1* | 11/2014 | Morse | A61L 27/3604 623/23.72 |

* cited by examiner

*Primary Examiner* — Yashita Sharma
(74) *Attorney, Agent, or Firm* — Woodard, Emhardt, Moriarty, McNett & Henry LLP

(57) ABSTRACT

Described are methods of performing a surgical tonsillectomy, medical devices for treating a void created by removing tonsil tissue from a patient, surgical kits, and use of an extracellular matrix material in the manufacture of a medicament for treating a surgical wound resulting from removal of tonsil tissue from a patient. Also described is a device for wound closure, and methods of making and using thereof.

18 Claims, 12 Drawing Sheets

TONSILLECTOMY SPONGE

REFERENCE TO RELATED APPLICATION

This application claims the benefit of priority of U.S. Patent Application Ser. No. 62/022,243 filed Jul. 9, 2014 which is hereby incorporated herein by reference in its entirety.

BACKGROUND

The present invention relates generally to medical devices, methods and materials, and in certain aspects to medical grafts, filling, or packing materials, and methods for the preparation and use thereof.

Many medical procedures required the treatment of the tissue defect in the patient, for example the defect can be either created surgically or present due to injury or disease. Examples occur in the removal of tonsils from a patient, which leaves a surgical defect in the region of the resected tonsil and associated tissue. Such defects may be left uncovered to heal, potentially with the aid of sutures to gather and close the defect. Tonsillectomies are conducted for a variety of reasons, including, for example, where a patient experiences frequent bouts of acute tonsillitis, has repeated bouts of peritonsillar abscess, has sleep apnea, has difficulty eating or swallowing due to enlarged or swollen tonsils, produces tonsilloliths in the back of their mouth, or has abnormally large tonsils with crypts. In certain practices, such defects are treated with a material that is applied to the defect and secured in place.

While some work has been done in this area, needs exist for improved and/or alternative medical graft, filling or packing devices, and associated methods. Certain aspects of the present invention are addressed to those needs.

SUMMARY

In certain aspects, the present disclosure provides unique methods and devices for treating a surgical void. In accordance with some forms of the disclosure, such surgical voids are created by removing tonsil tissue from a patient. Accordingly, in one embodiment, the present disclosure provides a surgical method comprising removing tonsil tissue from a patient so as to create a surgical void, and implanting a remodelable extracellular matrix foam material in the surgical void, the foam material effective to become infiltrated by native tissue. In one form, the extracellular matrix foam material comprises a dried remodelable extracellular matrix foam material. In certain inventive variants the extracellular matrix foam material is compressed such that the foam material expands when wetted. In some forms, the disclosed method includes the steps of partially closing the surgical void so as to create a pocket, and implanting the foam material within the pocket. Certain modes of practicing the disclosed method include the step of closing the surgical void over the implanted foam material. In certain embodiments, the remodelable extracellular matrix foam material retains at least one native growth factor from a source tissue and/or a non-native bioactive component. In one aspect, the remodelable extracellular matrix foam material comprises one or more of submucosal tissue, renal capsule membrane, dermal collagen, dura mater, pericardium, amnion, fascia lata, serosa, peritoneum or basement membrane.

In another embodiment, the disclosure provides a medical device for treating a surgical void created by removing tonsil tissue from a patient, the device comprising a remodelable extracellular matrix foam material effective to become infiltrated by native tissue and configured for implantation into the surgical void, such that when the foam material is placed within the surgical void the foam material allows for closure of the void over said foam material. In certain embodiments, the foam material comprises a dried remodelable extracellular matrix foam material. In some forms, the dried remodelable extracellular matrix foam material is compressed such that the foam material expands when wetted. Certain inventive variants comprises a molded remodelable extracellular matrix foam material. In certain embodiments, the remodelable extracellular matrix foam material retains at least one native growth factor from a source tissue and/or a non-native bioactive component. In one aspect, the remodelable extracellular matrix foam material comprises one or more of submucosal tissue, renal capsule membrane, dermal collagen, dura mater, pericardium, amnion, fascia lata, serosa, peritoneum or basement membrane.

In another embodiment, the present disclosure provides a surgical kit comprising a remodelable extracellular matrix foam material effective to become infiltrated by native tissue and configured for implantation into a surgical void caused by removal of tonsil tissue from a patient, and wherein the foam material is contained in a sterile package.

In another embodiment, the present disclosure provides a use of an extracellular matrix material in the manufacture of a medicament for treating a surgical wound resulting from removal of tonsil tissue from a patient, the medicament being in the form of a remodelable foam.

Additional embodiments, as well as features and advantages of embodiments of the invention will be apparent from the descriptions herein.

DETAILED DESCRIPTION OF THE ILLUSTRATED EMBODIMENTS

Figure 1:
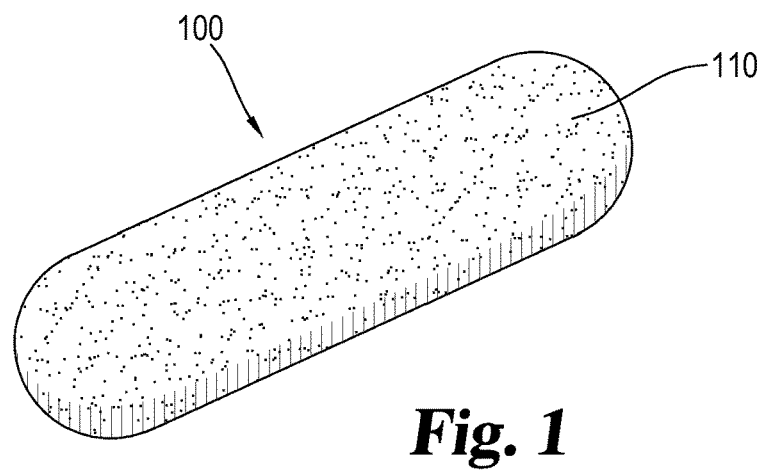
FIG. 1 is a perspective view of a medical device for treating a surgical void created by removing tonsil tissue from a patient.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail; although it will be apparent to those skilled in the relevant art that some features that are not relevant to the present invention may not be shown for the sake of clarity.

Figure 2:
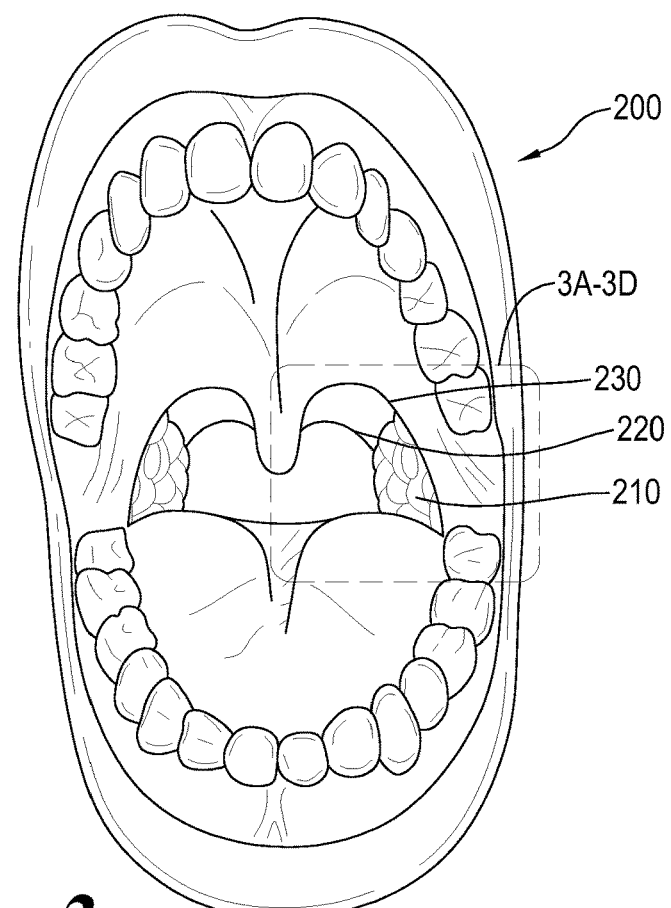
FIG. 2 is a view of a patient's mouth.

With reference to FIG. 2, shown is a patient's mouth 200 including tonsil tissue 210 between anterior tonsil pillar 230, and posterior tonsil pillar 220. As noted above, in some instances it is desirable to remove tonsil tissue 210. A tonsillectomy may be performed, for example, in response to: repeated occurrence of acute tonsillitis, obstructive sleep apnea, nasal airway obstruction, diphtheria carrier state, snoring, peritonsillar abscesses, dental malocclusion, bad breath, or where otherwise indicated. In some forms, tonsillectomy is performed by removing tonsil tissue from a patient resulting in a surgical void between the anterior tonsil pillar 230 and posterior tonsil pillar 220. As used in the present disclosure, tonsil tissue includes palatine tonsils, and adenoid or pharyngeal tonsils as well as surrounding tissues. In certain embodiments, the present disclosure provides a remodelable material for implantation into a surgical void resulting from a tonsillectomy procedure.

In use, certain embodiments of the medical device of the present disclosure provide a remodelable extracellular matrix foam material for use in surgical voids created by tonsillectomy, adenoidectomy, and/or tonsilloadenoidectomy. As will be discussed herein, such foam materials are configured to encourage angiogenesis and tissue infiltration of the surgical void, resulting in improved healing of the surgical void. The present disclosure also provides for sheet-form remodelable materials which can be used to close surgical voids created by tonsillectomy, adenoidectomy, and/or tonsilloadenoidectomy.

According to certain embodiments the present disclosure provides a surgical tonsillectomy method. In some forms, surgical tonsillectomy method comprises removing tonsil tissue from a patient so as to create a surgical void. In certain embodiments, tonsil tissue is removed, for example, using a scalpel, electrocautery, or radiofrequency ablation, although any method known to one having ordinary skill in the art for removing tonsil tissue is suitable. According to certain inventive variants the tonsillectomy method of the present disclosure also includes implanting a foam material into the surgical void. In some forms, the foam material comprises a remodelable foam material effective to become infiltrated by native tissues. As will be discussed herein, preferred materials include extracellular matrix materials. In some forms, the surgical tonsillectomy method also comprises closing the surgical void over the implanted foam material. The closing step can be performed by any suitable means including, for example, suturing.

Figure 3A:
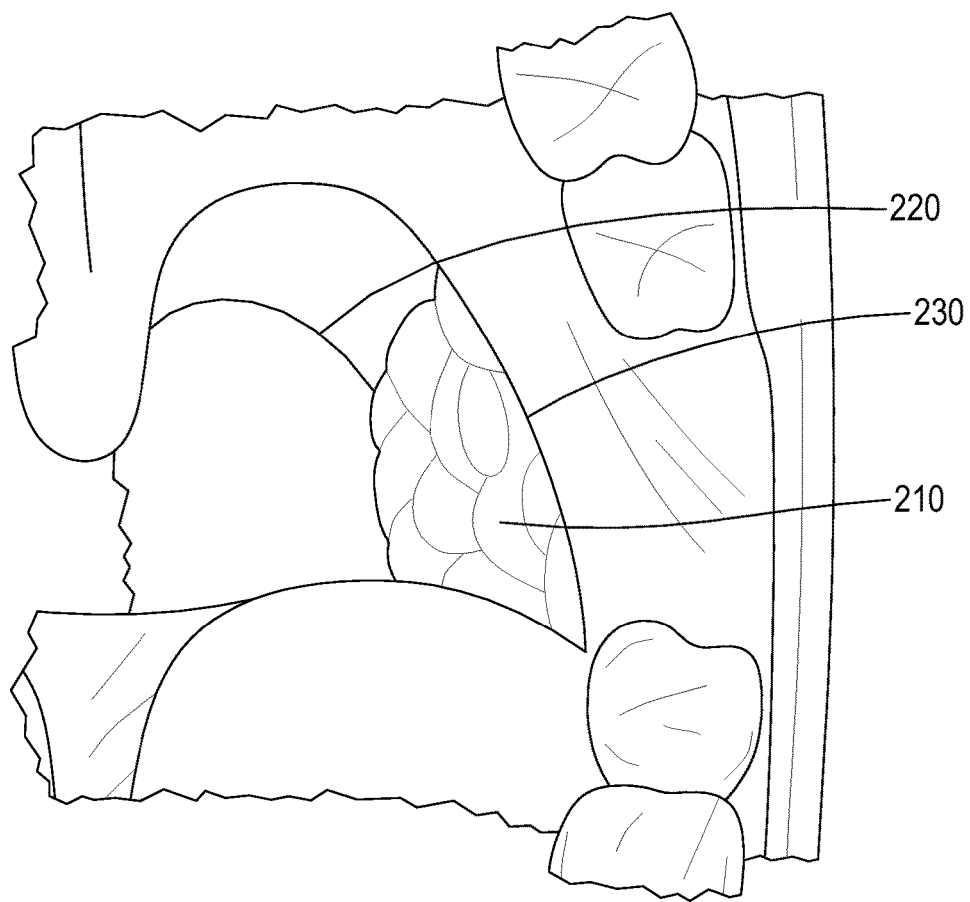
FIG. 3A is an expanded view of a patient's mouth.
Figure 3B:
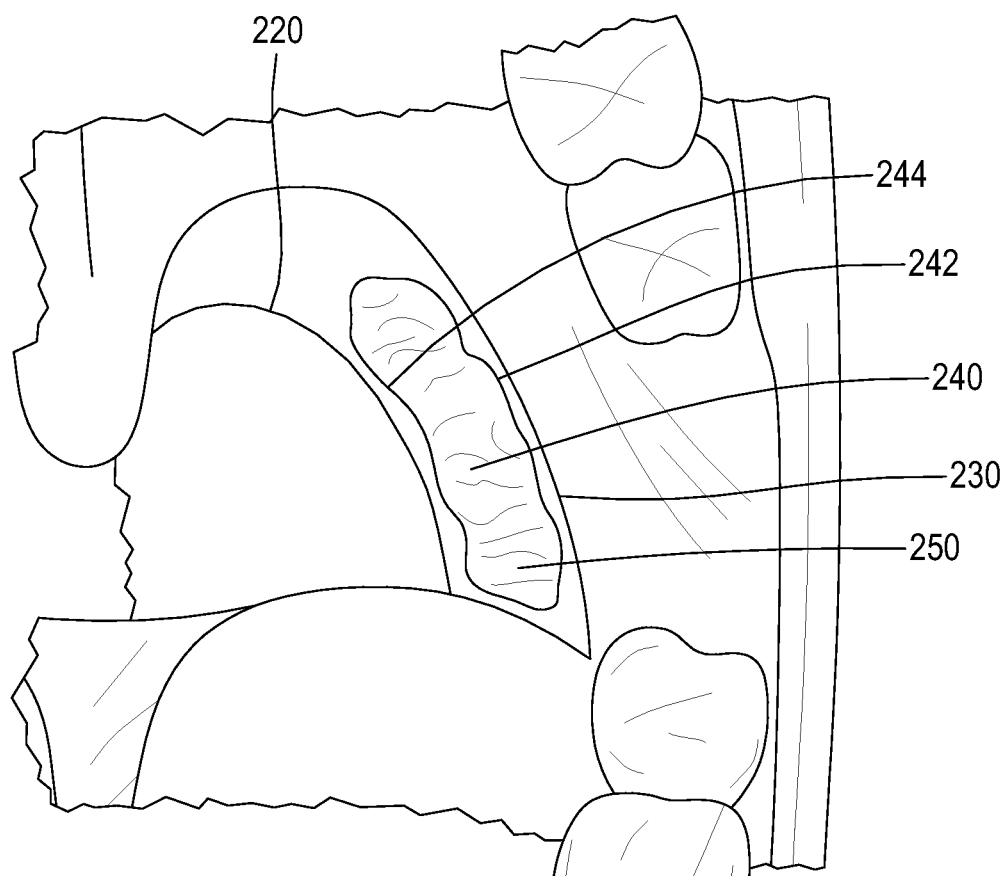
FIG. 3B is an expanded view of a patient's mouth, including a surgical void created by removal of tonsil tissue.
Figure 3C:
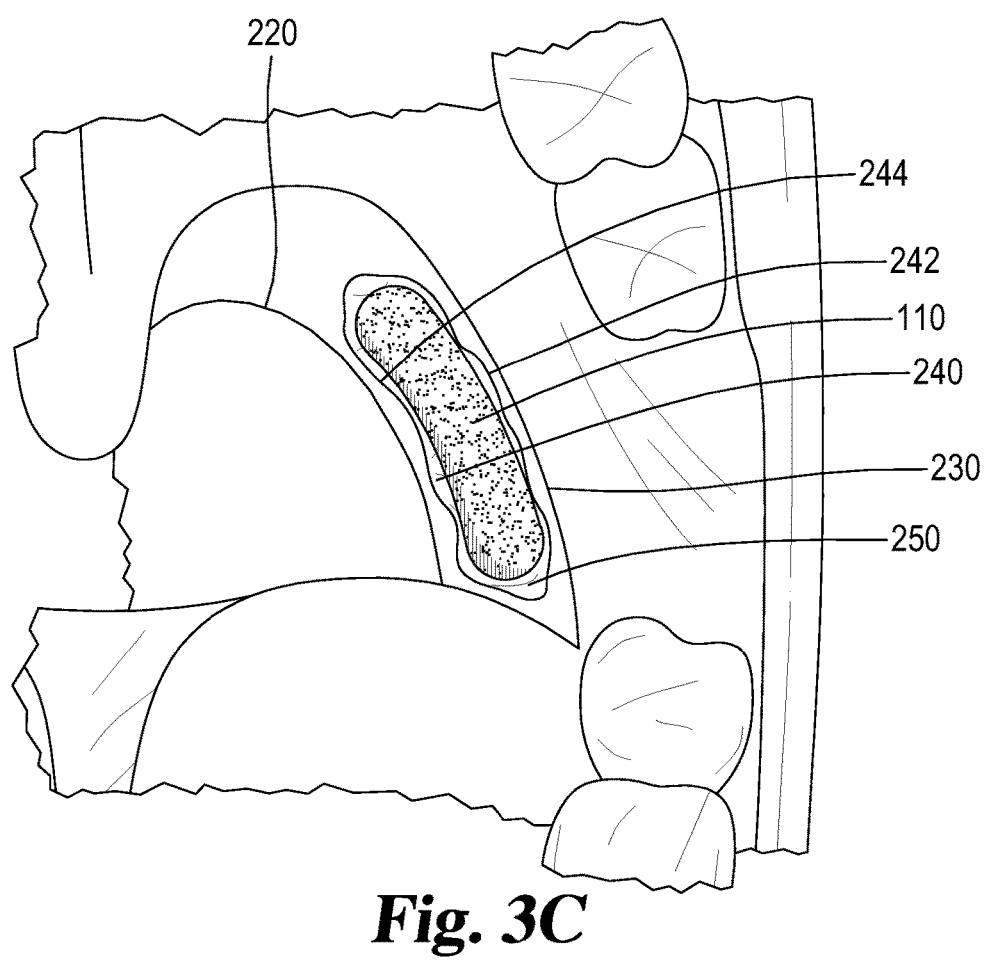
FIG. 3C is an expanded view of a patient's mouth, including a foam material implanted within a surgical void created by removal of tonsil tissue.
Figure 3D:
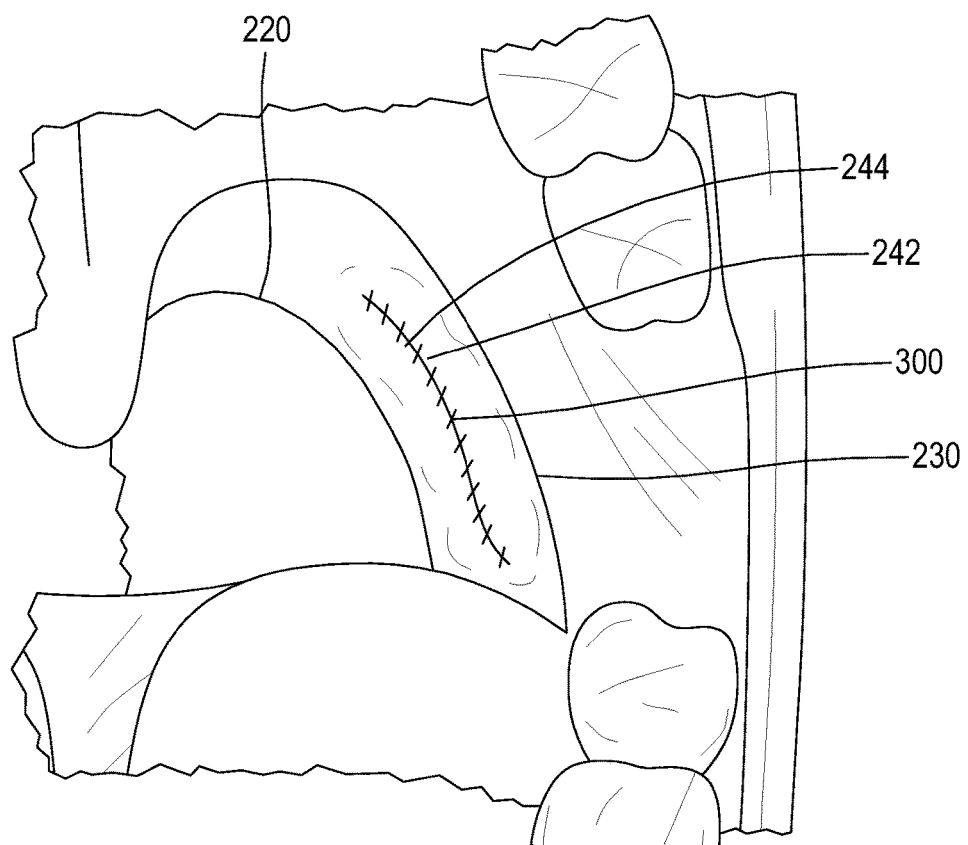
FIG. 3D is an expanded view of a patient's mouth, including a closed surgical void created by removal of tonsil tissue.

Referring now to FIGS. 3A-3D, shown is an expanded view of tonsil tissue 210 between anterior tonsil pillar 230 and posterior tonsil pillar 220. Briefly, FIG. 3B illustrates damaged tissue 250 forming a surgical void 240 created by removal of tonsil tissue from a patient. Surgical void 240 includes an anterior void edge 242 and a posterior void edge 244. FIG. 3C further illustrates foam material 110 implanted within surgical void 240. FIG. 3D illustrates sutures 300, pulling together anterior void edge 242 and posterior void edge 244 over foam material 110, closing surgical void 240.

The foam material of the present disclosure may be implanted by any means known to one having ordinary skill in the art. In one form, the foam material is placed directly into the surgical void created by removal of tonsil tissue such that the foam material contacts the damaged tissue therein. In certain embodiments, the foam material is delivered by a device configured to deploy the foam material within the surgical void created by removal of tonsil tissue. As will be discussed herein, in some forms the foam material comprises a dried material such that upon contact with fluid, for example blood, the foam material swells to fill, or substantially fill, the surgical void created by removal of patient tissue. In some forms, the foam material comprises a comminuted powder or particulate ECM material, such that the comminuted foam material is packed into the void created by removal of tonsil tissue.

Figure 4:
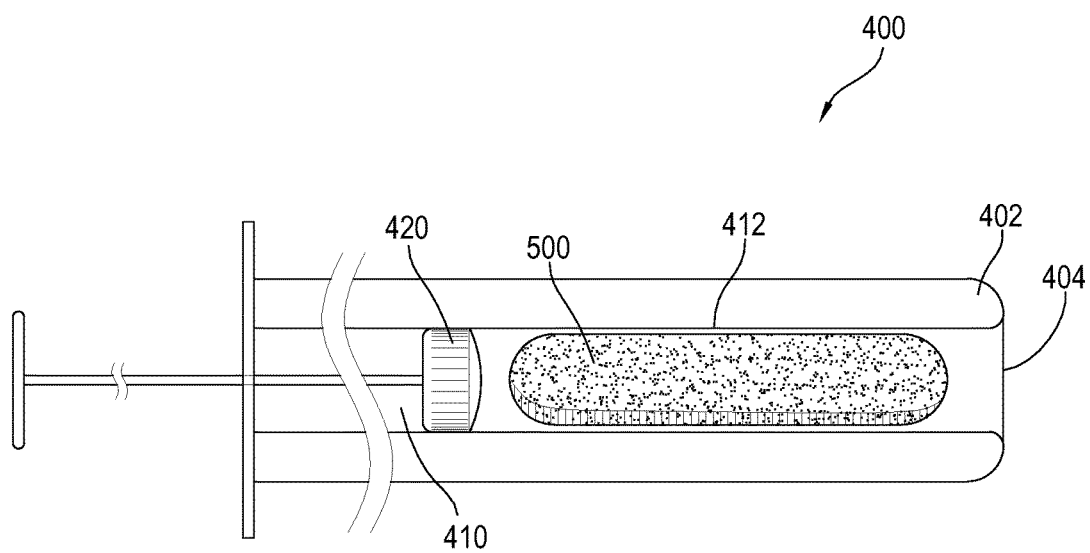
FIG. 4 is a perspective view of one embodiment of a foam material of the present disclosure contained within a cannulated deployment device.

As described above, in certain embodiments, the foam material is delivered by a deployment device configured to deploy the foam material into a surgical void created by removal of tonsil tissue. In some forms, the deployment device comprises a cannulated device having a lumen and a deployment mechanism. With reference now to FIG. 4, in the illustrated embodiment the deployment device comprises a cannulated device 400 having a lumen 410, inner surface 412, and plunger 420. The illustrated embodiment also includes deployment end 402 including opening 404. In certain embodiments, plunger 420 is configured to push foam material 500 through opening 404. In some forms, opening 404 is sealed prior to passage of foam material 500 through opening 404. In certain embodiments, the foam material 500 is compressed and loaded within lumen 410 of deployment device 400. In some forms, the compressed foam material is delivered within the cannulated device to a void created by removal of tonsil tissue and the foam material is deployed from the cannulated device into the void. In accordance with certain inventive variants, the foam material is compressed and loaded within a deployment device. Certain inventive variants include a cannulated delivery device and a dried compressed foam material sealed in a sterile package.

Figure 5A:
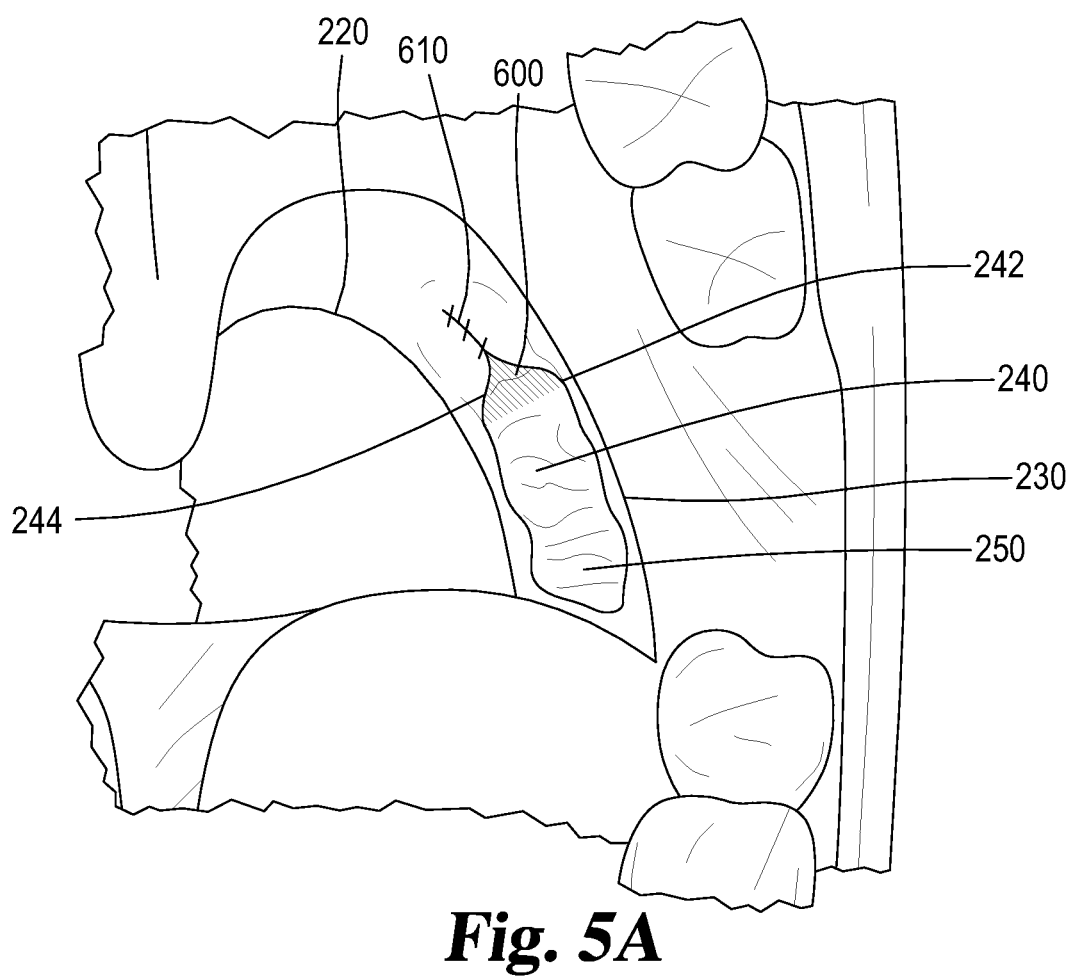
FIG. 5a is an expanded view of a patient's mouth, including a partially closed surgical void created by removal of tonsil tissue.
Figure 5B:
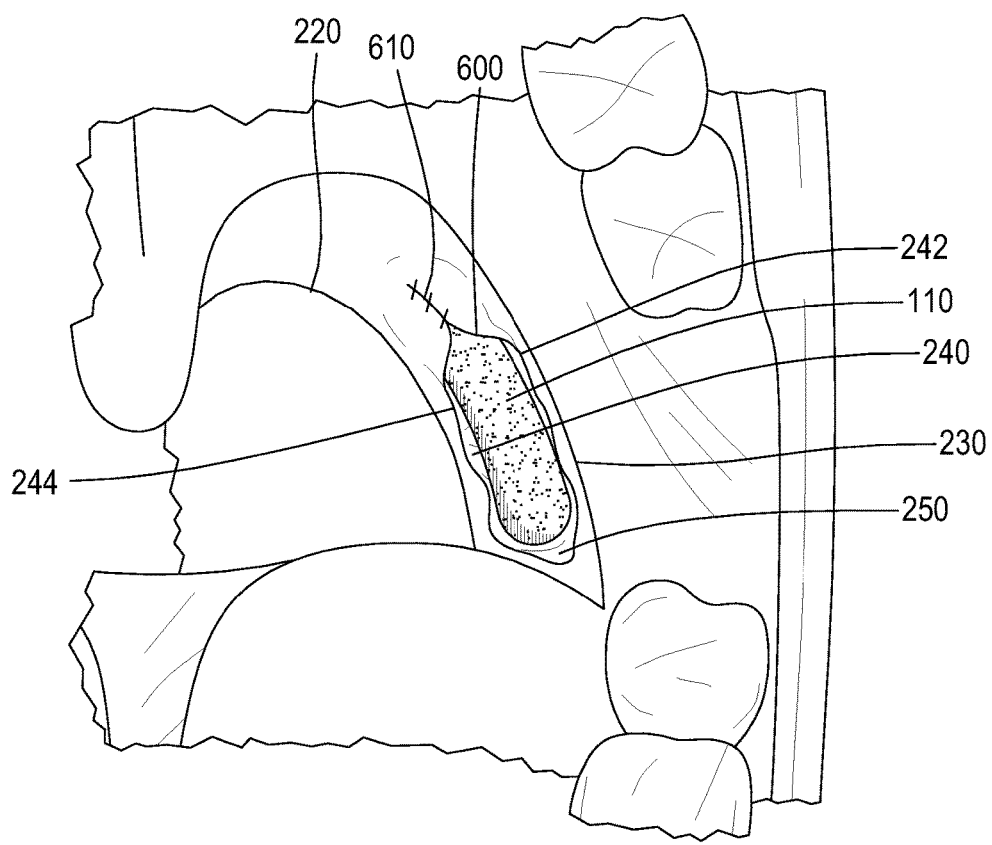
FIG. 5b is an expanded view of a patient's mouth, including a foam material implanted within a partially closed surgical void created by removal of tonsil tissue.

With reference now to FIGS. 5a-5b, illustrated is an expanded view of damaged tissue 250 forming a surgical void 240 created by removal of tonsil tissue from a patient. In the illustrated embodiment, surgical void 240 includes an anterior void edge 242 and a posterior void edge 244. In the illustrated embodiment surgical void 240 resides between anterior tonsil pillar 230 and posterior tonsil pillar 220. Certain inventive methods include partially closing the surgical void or wound so as to create a pocket 600. In certain embodiments, anterior void edge 242 and a posterior void edge 244 are partially sutured together to create partial closure 610. In some forms, the foam material 110 is receivable within the pocket so as to retain the foam material within the surgical void. The foam material can be delivered to the void by any means described herein, including for example, through a cannulated deployment device. According to some forms of practicing the disclosed method, after the foam material is placed within the pocket the void is closed over the foam material, for example as illustrated in FIG. 3D.

In some forms, the present disclosure includes closing the surgical void over the implanted foam material. In accordance with some forms of practicing the disclosed methods, the anterior void edge and the posterior void edge are secured together substantially sealing the implanted sealing material within the void created by removal of tonsil tissue. Void edges can be secured by any means known to one having skill in the art, for example, sutures, staples, and/or glue.

According to certain embodiments the present disclosure provides wound closure devices. In some forms, the wound closure device of the present disclosure comprises a remodelable material as disclosure herein. The remodelable material may comprise, for example, a foam or sheet-form material. In certain embodiments the wound closure device is configured to attach to patient tissue, for example via sutures, staples, and/or a bioadhesive. In some forms the wound closure device has at least one surface coated with a bioadhesive. Suitable bioadhesives for use with the presently described device include but are not limited to acrylate and/or fibrin glue. In some forms, the wound closure device is configured such that the bioadhesive can adhere to patient tissue within or around a tissue defect. In certain embodiments, the wound closure device is a sheet-like construct including a first surface opposing a second surface, and a first lateral side opposite a second lateral side. A bioadhesive may be applied to all or part of the first surface and/or all or part of the second surface. The wound closure device is also configured to adopt an open position in which the first lateral side and second lateral side are spaced apart, and a closed position is with the first lateral side and second lateral side are brought together.

In use, the wound closure device of the present disclosure is implanted within a tissue defect (e.g. a void created by removal of tonsil tissue). Upon implantation the wound closure device is secured within the tissue defect. In certain embodiments the wound closure device is secured within the tissue void by an adhesive coating on the surface contacting patient tissue. The lateral sides of the wound closure device may then be brought together and secured closing the tissue defect. In certain embodiments, the second surface which is facing away from patient tissue includes a bioadhesive configured to secure the wound closure device in the closed position. In certain embodiments the bioadhesive has sufficient strength so as to remain adhered to patient tissue while the two sides of the wound closure device are brought together. In this way it is envisioned that the wound closure device of the present disclosure may be used without additional securing means. In some forms, sutures and/or staples may be used to secure the wound closure device to patient tissue and/or in the closed position.

In certain embodiments the wound closure device includes certain adaptations to facilitate implantation. For example the wound closure device may contain one or more tabs positioned at or near the first lateral side and the second lateral side. The tabs are configured to provide a surface for the surgeon to grasp in order to close the wound (i.e. bring the sides together). The tabs may also provide a surface in which the surgeon may apply a suture to secure the wound closure device in the closed position. It is envisioned that the tabs may comprise the same remodelable material as the wound closure device. It is also envisioned that the tabs comprise a biocompatible material such as a suture. In certain embodiments one or more of the tabs includes an attached suture to facilitate closing.

Wound closure devices of the present disclosure may be used alone or in conjunction with further materials. For example, in certain embodiments a foam material as described herein may be implanted with a wound closure device. In certain embodiments the foam material is adhered to the wound closure device prior to, during, or after implantation of the wound closure device. In some modes of practicing the disclosed methods a foam material is packed within the surgical void such that upon closure of the wound closure device the foam material becomes enclosed within the wound closure device. Such embodiments may be useful, for example, to provide additional tissue bulk and/or deliver beneficial bioactive components.

In certain embodiments the present disclosure provides wound closure devices having a plurality of perforations therethrough. In some forms such perforations allow for fluid and/or cellular flow through the wound closure device so as to enhance cellular infiltration of the implanted material. When present the perforations may be configured to extend through the remodelable material thus creating a passage for fluid and/or cellular infiltration. In other embodiments the perforations may be configured to extend only partially through the wound closure device, for example in a layered device perforations may extend through a portion of the layers but not all of the layers.

Figure 6:
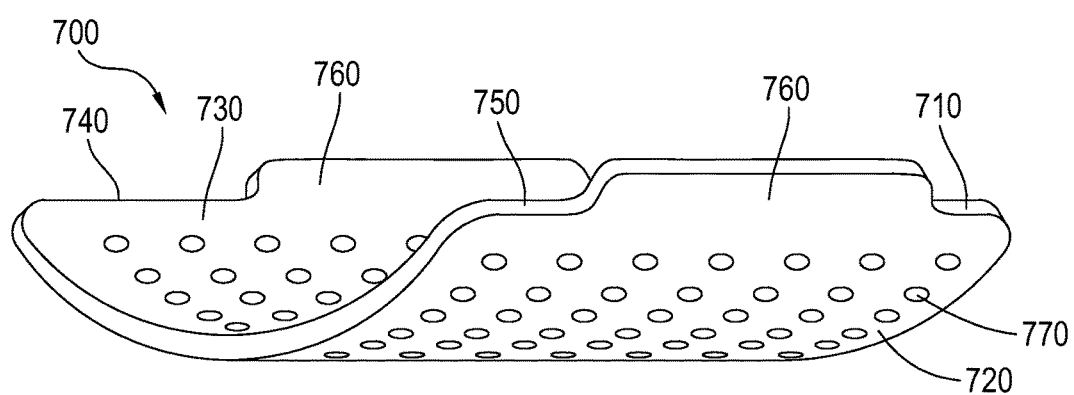
FIG. 6 is a perspective view of a wound closure device for treating a surgical void created by removing tonsil tissue from a patient.

Turning now to the embodiment illustrated by FIG. 6, shown is one embodiment of a wound closure device 700. In the illustrated embodiment wound closure device 700 comprise a remodelable material 710 having a first surface 720 opposing a second surface 730 and a first lateral side 740 opposing a second lateral side 750. The illustrated embodiment also includes tabs 760, in the illustrated embodiment tabs 760 are contiguous with and comprise extensions of the remodelable material 710. The illustrated embodiment also features perforations 770.

According to certain embodiments the present disclosure provides a surgical tonsillectomy method. In some forms, surgical tonsillectomy method comprises removing tonsil tissue from a patient so as to create a surgical void. In certain embodiments, tonsil tissue is removed, for example, using a scalpel, electrocautery, or radiofrequency ablation, although any method known to one having ordinary skill in the art for removing tonsil tissue is suitable. According to certain inventive variants the tonsillectomy method of the present disclosure also includes implanting a remodelable wound closure device into the surgical void. In some forms, the wound closure device comprises a remodelable material effective to become infiltrated by native tissues. As will be discussed herein, preferred materials include extracellular matrix materials. In some forms, the surgical tonsillectomy method further comprises closing the surgical void by pulling a first side and a second side of the wound closure device together. The surgical tonsillectomy method may then comprise securing the wound closure device in the closed position. The securing step can be performed by any suitable means including, for example, suturing.

Figure 7A:
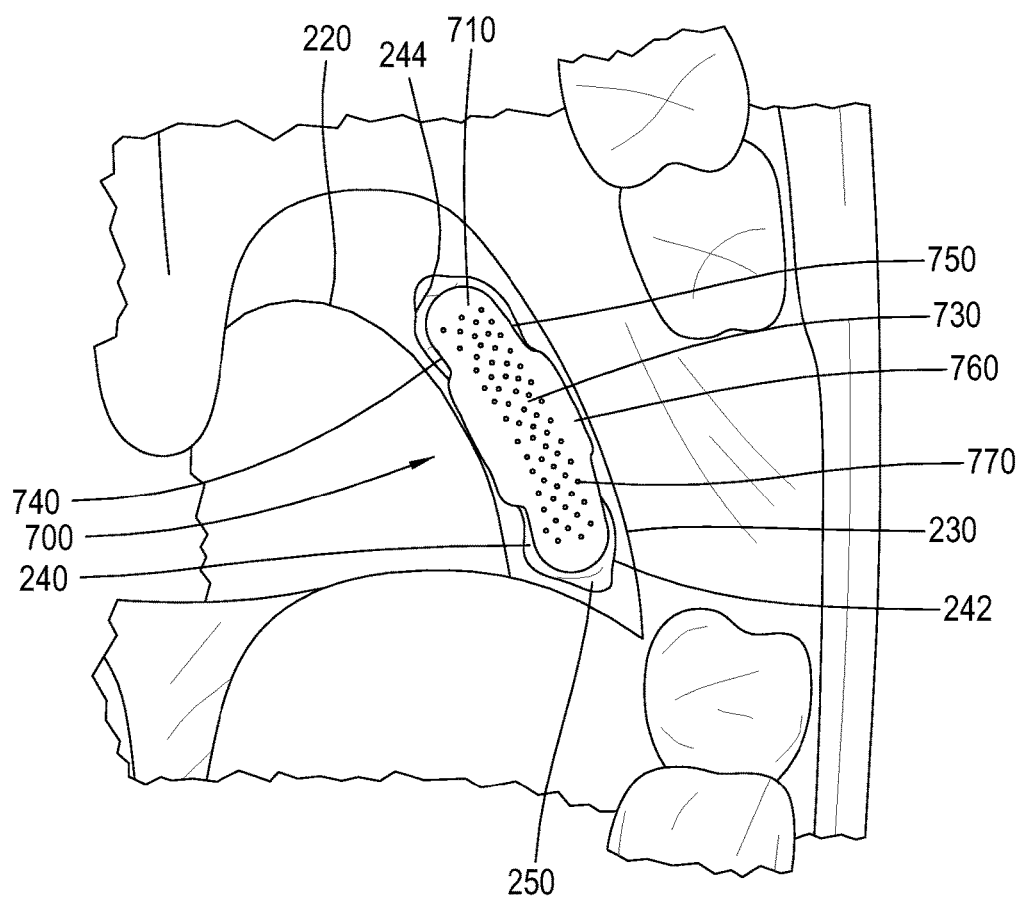
FIG. 7A is an expanded view of a patient's mouth, including a wound closure device implanted within a surgical void created by removal of tonsil tissue.
Figure 7B:
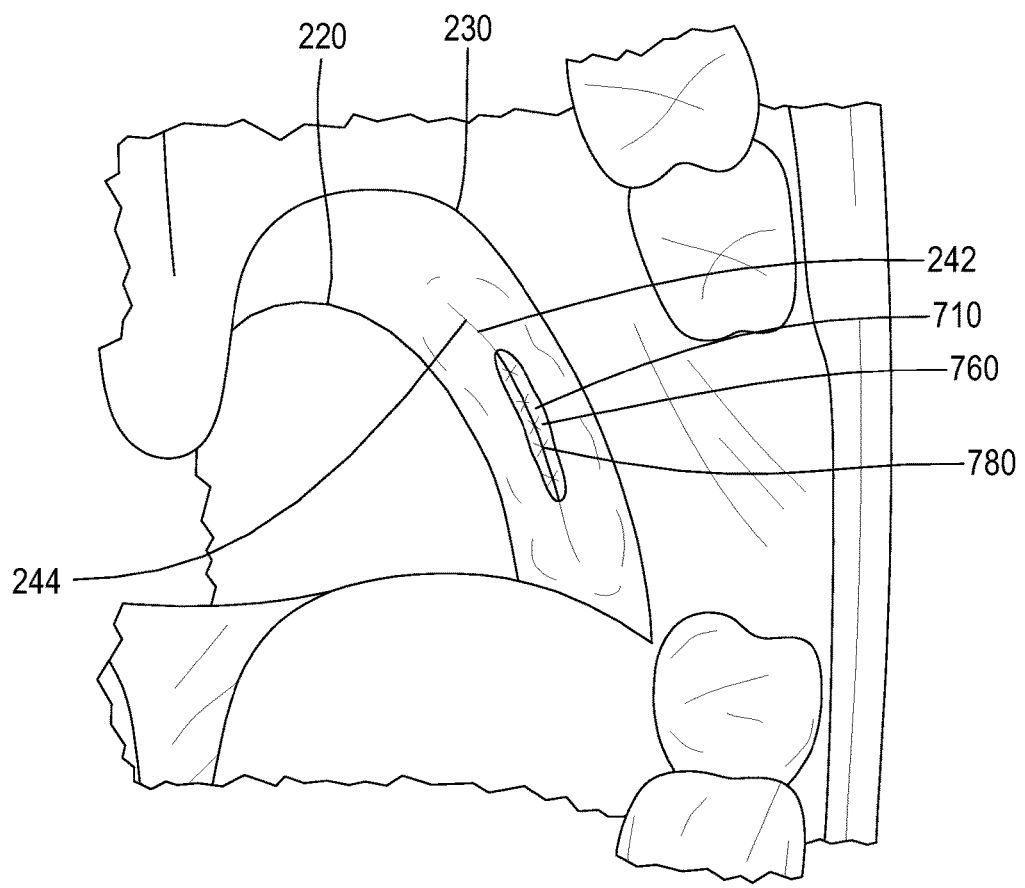
FIG. 7B is an expanded view of a patient's mouth, including a closed surgical void created by removal of tonsil tissue.

Referring now to FIGS. 7A and 7B, shown is an expanded view of a damaged tissue 250 forming a surgical void 240 caused by the removal of tissue between posterior tonsil pillar 220 and anterior tonsil pillar 230. FIG. 7A illustrates a wound closure device 700 implanted within the surgical void 240. FIG. 7B illustrates a closed surgical void in which anterior void edge 242 and posterior void edge 244 have been brought together. FIG. 7B further illustrates tab(s) 760 protruding from the wound closure and containing attachment means 780 which function to secure the wound closure device in a closed position. In the illustrated embodiment attachment means 780 comprise sutures. In the illustrated embodiment the wound closure device is sized such that upon wound closing much of the device is encased within patient tissue. It is however envisioned that it may be desirable in certain applications, for example when additional attachment means are desired, to provide a graft such that the first and/or second lateral sides protrude from the wound closure when in the closed position. Such protruding material may be further secured or trimmed off by the surgeon.

In certain embodiments a wound closure device as taught herein may be implanted with a foam material as taught herein. For example, in some forms the wound closure device is implanted within a surgical void and a foam material is implanted onto the wound closure device such that the wound closure device envelopes all or part of the foam material when the wound closure device adopts a closed or folded position. In certain embodiments, all or part of the wound closure device may comprise a foam material as taught herein.

Figure 8A:
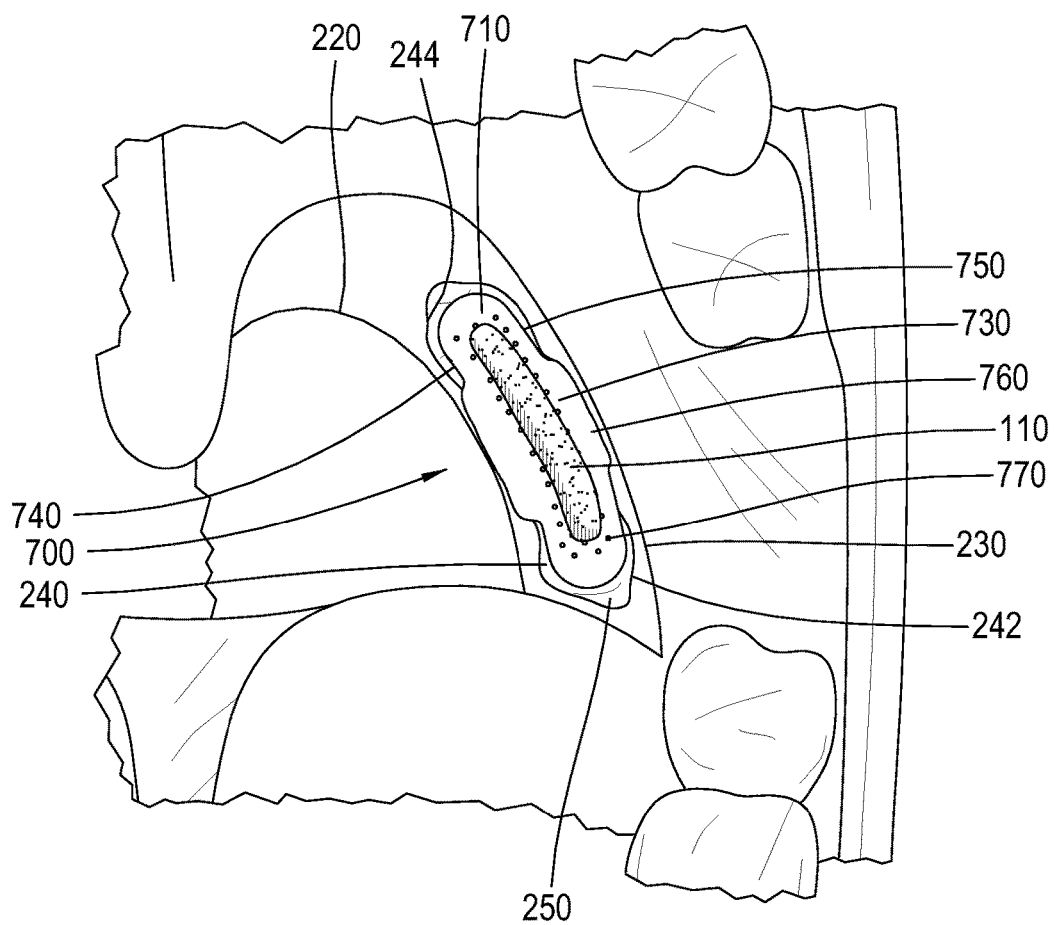
FIG. 8A is an expanded view of a patient's mouth, including a wound closure device and a foam material implanted within a surgical void created by removal of tonsil tissue.
Figure 8B:
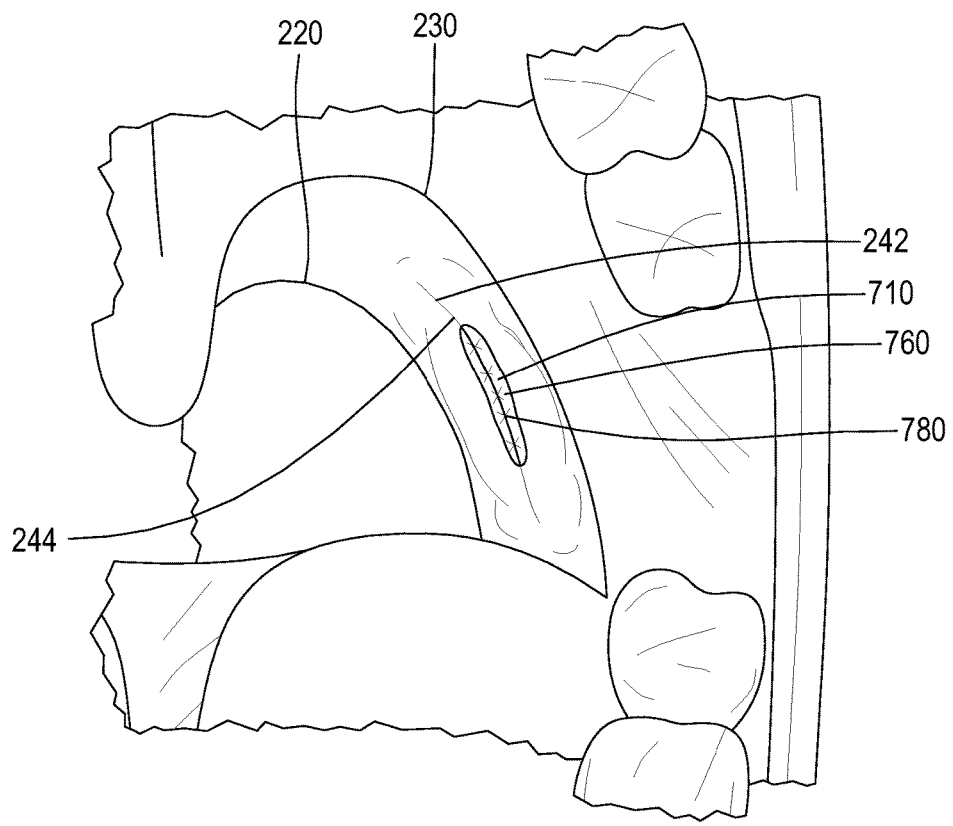
FIG. 8B is an expanded view of a patient's mouth, including a closed surgical void created by removal of tonsil tissue.

Referring now to FIGS. 8A and 8B, shown is an expanded view of a damaged tissue 250 forming a surgical void 240 caused by the removal of tissue between posterior tonsil pillar 220 and anterior tonsil pillar 230. FIG. 8A illustrates a wound closure device 700 and foam material 110 implanted within the surgical void 240. FIG. 8B illustrates a closed surgical void in which anterior void edge 242 and posterior void edge 244 have been brought together. FIG. 8B further illustrates tab(s) 760 protruding from the wound closure and containing attachment means 780 which function to secure the wound closure device in a closed position. In the illustrated embodiment attachment means 780 comprise sutures. In the illustrated embodiment the wound closure device is sized such that upon wound closing much of the device is encased within patient tissue. It is however envisioned that it may be desirable in certain applications, for example when additional attachment means are desired, to provide a graft such that the first and/or second lateral sides protrude from the wound closure when in the closed position. Such protruding material may be further secured or trimmed off by the surgeon.

Figure 9:
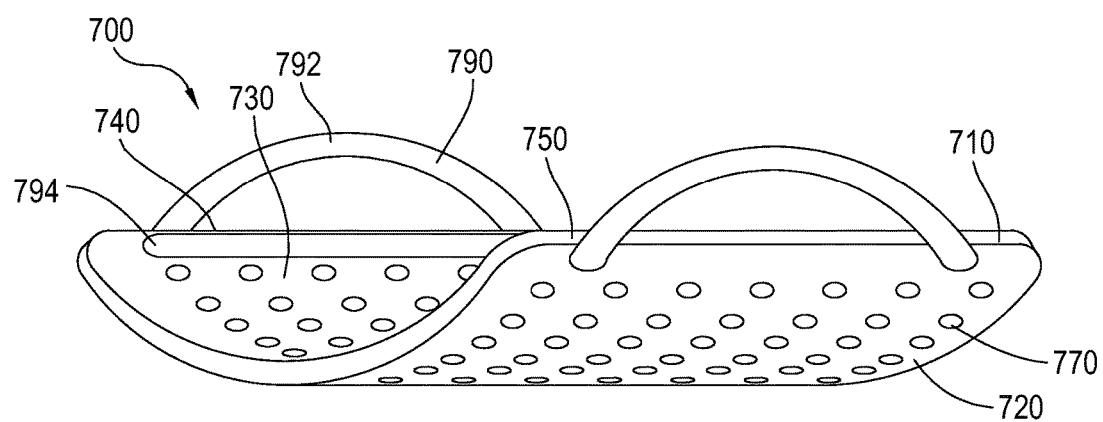
FIG. 9 is a perspective view of a wound closure device for treating a surgical void created by removing tonsil tissue from a patient.

Turning now to FIG. 9, shown is one embodiment of a wound closure device 700. In the illustrated embodiment wound closure device 700 comprise a remodelable material 710 having a first surface 720 opposing a second surface 730 and a first lateral side 740 opposing a second lateral side 750. The illustrated embodiment also includes closure members 790, in the illustrated embodiment closure members 790 comprise an elongate string-like element, for example a suture or biodegradable cord. In accordance with certain inventive variants, the closure member contains a first portion 792 extending beyond the sides of the remodelable material, and a second portion 794 slidably associated with the first portion such that the device may be brought from an open position to a closed position by pulling the closure member.

In certain embodiments, the foam and/or wound closure device will be comprised of a remodelable material. Particular advantage can be provided by devices that incorporate a remodelable collagenous material. Such remodelable collagenous materials, whether reconstituted or naturally derived, can be provided, for example by collagenous materials isolated from a warm-blooded vertebrate, especially from a mammal. Such isolated collagenous material can be processed so as to have remodelable angiogenic properties and promote cellular invasion and ingrowth. Remodelable materials may be used in this context to promote cellular growth on around and/or in bodily regions in which inventive devices are implanted or engrafted.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

The ECM tissue material utilized desirably retains a structural microarchitecture from the source tissue, including structural fiber proteins such as collagen and/or elastin that are non-randomly oriented. Such non-random collagen and/or other structural protein fibers can in certain embodiments provide an ECM tissue that is non-isotropic in regard to tensile strength, thus having a tensile strength in one direction that differs from the tensile strength in at least one other direction.

The ECM tissue material may include one or more bioactive agents. Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, and protein or gene expression.

Submucosa-containing or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufactured step, immediately prior to the procedure (e.g., by soaking the material in a solution containing a suitable antibiotic such as cefazolin), or during or after engraftment of the material in the patient.

Inventive devices can incorporate xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

In certain forms, inventive devices include a material receptive to tissue ingrowth. Upon deployment of such devices in accordance with the present invention, cells from the patient can infiltrate the material, leading to, for example, new tissue growth on, around, and/or within the device. In some embodiments, the device comprises a remodelable material. In these embodiments, the remodelable material promotes and/or facilitates the formation of new tissue, and is capable of being broken down and replaced by new tissue. In certain embodiments, the implanted device contracts in response to ingrowth of patient tissue. Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, any component of a tonsillectomy graft material of the invention (including any ECM material) can have a level or degree of porosity. In certain embodiments, the porosity of a layer of ECM material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular application or procedure.

It is sometimes advantageous to perform drying operations under relatively mild temperature exposure conditions that minimize deleterious effects upon the ECM materials of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

In additional embodiments, graft elements useful in the invention can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a bodily segment within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typically such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of three-dimensionally stable shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

In addition to the above, the expanded collagenous material of the present invention can be used to prepare a molded or shaped construct for example a sponge. Suitable sponge form ECM materials for use in this aspect of the disclosure can be prepared, for example, as described in U.S. patent application Ser. No. 12/489,199 published Dec. 31, 2009, which is herein incorporated by reference in its entirety. The method for preparing such device comprises providing an expanded collagenous material, comminuting the expanded material, casting the expanded collagenous material into a shape, and freezing and/or lyophilizing the cast, expanded collagenous material to form the construct. In certain embodiments the construct is crosslinked. Freezing can be done at a temperature of about −80° C. for about 1 to about 4 hours, and lyophilization can be performed for about 8 to about 48 hours. Typically, the material used to prepare the construct is an expanded collagenous material that has been replenished with one or more bioactive components. The expanded collagenous material can be cast into any shape desired and will typically be shaped by a skilled artisan to fill an intended void, such as for example a void caused by removal of tonsil tissue from a patient. In preferred embodiments, a sponge is formed and is used, for example, to fill a void in a tissue (e.g., organ tissue) after surgery. When a sponge form construct is prepared, the lyophilized, expanded remodelable collagenous material can be compressed and loaded into a deployment device for delivery into a patient. Once delivered, the device can expand to substantially fill or occlude the area in which it was deployed. Suitable deployment devices will be generally known to those of ordinary skill in the art and include, for example, delivery catheters and the like.

In certain embodiments, an expanded collagenous material, in any form, can be crosslinked. An expanded collagenous material can be crosslinked either before or after it is formed into a medical device, or both. Increasing the amount (or number) of crosslinkages within the material or between two or more layers of the material can be used to enhance its strength. However, when a remodelable material is used, the introduction of crosslinkages within the material may also affect its resorbability or remodelability. Consequently, in certain embodiments, a remodelable collagenous material will substantially retain its native level of crosslinking, or the amount of added crosslinkages within the medical device will be judiciously selected depending upon the desired treatment regime. In many cases, the material will exhibit remodelable properties such that the remodeling process occurs over the course of several days or several weeks. In certain preferred embodiments, the remodeling process occurs within a matter of about 5 days to about 12 weeks. With regard to a sponge form construct, crosslinking of a compressed construct may promote re-expansion of the construct after implantation into a patient.

With regard to compressible/expandable plugs, sponges or other constructs as described herein, expansion additives and/or crosslinking can be used to impart desirable compression/re-expansion properties. In preferred forms, the constructs are capable of volumetric compression when dry at a ratio of at least 10:1 (i.e. the compressed form occupies no more than 10% of its original, relaxed and unexpanded volume), more preferably at a ratio of at least 20:1. At the same time, in preferred forms, the compressed constructs are capable of re-expansion to substantially their original volume (e.g. at least about 80% of their original volume, more preferably at least 90%, and most preferably at least 95%) within about 30 seconds when delivered in their dry, compressed form into a volume of water.

For use in the present invention, introduced crosslinking of the expanded remodelable collagenous material may be achieved by photo-crosslinking techniques, or by the application of a crosslinking agent, such as by chemical crosslinkers, or by protein crosslinking induced by dehydration or other means. Chemical crosslinkers that may be used include for example aldehydes such as glutaraldehydes, diimides such as carbodiimides, e.g., 1-ethyl-3-(3-dimethylaminopropyl)carbodiimide hydrochloride (EDC), diisocyanates such as hexamethylene-diisocyanate, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression similar to a non-expanded collagenous material.

Expanded collagenous materials can be used to prepare a wide variety of graft elements useful in certain inventive devices. Methods for preparing such elements can include contacting an ECM or other collagenous starting material with an alkaline substance in an amount effective to expand the material, casting or otherwise forming the expanded collagenous material into a particular shape (e.g. an elongate tube or cylinder or a plug-like segment), and lyophilizing the expanded material to form a dried graft body.

ECM tissue layers can be used in the manufacture of laminated graft body structures, For these purposes each bioresorbable sheet can for example be comprised of about 1 to 10 extracellular matrix tissue layers. Illustratively, either bioresorbable sheet can include only a single ECM tissue layer, and the other may include multiple (e.g. 1 to 10, or 2 to 6) ECM tissue layers. Sheets of multilaminate ECM tissue layers can be prepared in any suitable fashion. These include, for instance, dehydrothermal bonding under heated, non-heated or lyophilization conditions, using adhesives, glues or other bonding agents, stitching, crosslinking with chemical agents or radiation (including UV radiation), or any combination of these with each other or other suitable methods. For additional information as to techniques for laminating ECM layers to one another, reference may be made for example to U.S. Pat. Nos. 5,711,969, 5,755,791, 5,855,619, 5,955,110, 5,968,096, and to U.S. Patent Publication No. 20050049638.

With reference now to FIG. 1, shown is one embodiment of a medical device for treating a surgical void created by removing tonsil tissue from a patient. In some forms, device 100 comprises foam material 110 configured for implantation into a surgical void created by removal of tonsil tissue from a patient. In the illustrated embodiment, device 100 comprises a generally cylindrical plug-like body sized and configured for implantation into a surgical void created by removal of tonsil tissue from a patient. As described above, extracellular matrix tissues can be processed in a variety of ways to form device 100. For example, in some forms device 100 comprises an extracellular matrix material that has been contacted with an alkaline substance sufficient to form an expanded extracellular matrix foam material. According to certain inventive variants, such foam materials may be compressed or cast to form a medical device sized and configured for implantation into a surgical void created by removal of tonsil tissue. It is also envisioned that the foam material may comprise a sheet form, layered, comminuted, and/or powdered extracellular matrix foam material.

As illustrated in FIG. 3B, surgical void 240 created by removal of tonsil tissue may be generally oblong, extending between anterior tonsil pillar 230 and posterior tonsil pillar 220. However, it is envisioned that foam material 110 can be sized and configured to fit a variety of surgical voids which may vary according to patient morphologies or the technique utilized to remove tonsil tissue. It is envisioned that prior to implanting foam material 110 a physician may modify the material, for example trimming the material to fit within a particular surgical void.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected.

What is claimed is:

1. A surgical tonsillectomy method, comprising:
   removing tonsil tissue from a patient, so as to create a surgical void;
   implanting a wound closure device in the surgical void, the wound closure device comprising a remodelable sheet having a first edge and a second edge and a first surface between the first edge and the second edge and a second surface opposing the first surface, wherein the sheet is configurable from an open condition wherein the first edge and the second edge are spaced apart to a closed condition wherein the first edge and the second edge are brought together;
   implanting a remodelable extracellular matrix foam material in the surgical void, said foam material effective to become infiltrated by native tissue; and
   manipulating the remodelable sheet from said open position to said closed position to close the surgical void.

2. The method of claim 1, wherein said extracellular matrix foam material comprises a dried remodelable extracellular matrix foam material.

3. The method of claim 2, wherein said dried remodelable extracellular matrix foam material is compressed such that said foam material expands when wetted.

4. The method of claim 1, further comprising closing the surgical void over the implanted foam material.

5. The method of claim 1, wherein the remodelable extracellular matrix foam material retains at least one native growth factor from a source tissue.

6. The method of claim 1, wherein the remodelable extracellular matrix foam material comprises one or more of submucosal tissue, renal capsule membrane, dermal collagen, dura mater, pericardium, amnion, fascia lata, serosa, peritoneum or basement membrane.

7. The method of claim 1, wherein the remodelable extracellular matrix foam material further comprises a non-native bioactive component.

8. The method of claim 1, further comprising partially closing the void so as to create a pocket, and wherein said implanting comprises delivering the foam material within said pocket.

9. The method of claim 8, further comprising closing the surgical void over the implanted foam material.

10. The method of claim 1, wherein the sheet is implanted into the surgical void and the extracellular matrix foam material is implanted onto the sheet.

11. The method of claim 10, wherein the sheet and the extracellular matrix foam material are sized and configured such that the sheet envelopes the extracellular matrix foam material when the sheet is in the closed condition.

12. The method of claim 1, further comprising a bioadhesive on the second surface of the sheet configured to adhere to patient tissue.

13. The method of claim 1, further comprising a bioadhesive on the first surface of the sheet configured to secure the sheet in said closed position.

14. The method of claim 1, wherein the remodelable sheet comprises an extracellular matrix material.

15. The method of claim 14, wherein the extracellular matrix material retains one or more bioactive agents native to a source tissue for the extracellular matrix material.

16. The method of claim 14, wherein said extracellular matrix material comprises one or more of submucosal tissue, renal capsule membrane, dermal collagen, dura mater, pericardium, amnion, fascia lata, serosa, peritoneum or basement membrane.

17. The method of claim 1, wherein said manipulating causes said remodelable sheet to envelope said extracellular matrix foam material.

18. The method of claim 1, the remodelable sheet having a plurality of perforations extending through the sheet from the first side to the second side.

* * * * *